(12) United States Patent
Clark

(10) Patent No.: US 9,104,046 B1
(45) Date of Patent: Aug. 11, 2015

(54) APPARATUS FOR AND METHODS OF DETERMINING IF PROGRESSIVE ADD LENSES (PALS) ARE PROPERLY POSITIONED IN A SUBJECT'S EYEGLASSES

(71) Applicant: Thomas H Clark, Colchester, VT (US)

(72) Inventor: Thomas H Clark, Colchester, VT (US)

( * ) Notice: Subject to any disclaimer, the term of this patent is extended or adjusted under 35 U.S.C. 154(b) by 0 days.

(21) Appl. No.: 14/164,491

(22) Filed: Jan. 27, 2014

(51) Int. Cl.
  *A61B 3/10* (2006.01)
  *A61B 3/00* (2006.01)
  *G02C 13/00* (2006.01)
  *A61B 3/02* (2006.01)

(52) U.S. Cl.
  CPC ............ *G02C 13/005* (2013.01); *A61B 3/0008* (2013.01); *A61B 3/02* (2013.01)

(58) Field of Classification Search
  USPC .................................................. 351/200–246
  See application file for complete search history.

(56) References Cited

U.S. PATENT DOCUMENTS

| | | | |
|---|---|---|---|
| 7,300,153 B2 * | 11/2007 | Wehner et al. | 351/159.42 |
| 2008/0316427 A1 * | 12/2008 | Fisher et al. | 351/233 |
| 2009/0290125 A1 * | 11/2009 | Varnas et al. | 351/246 |
| 2010/0283965 A1 * | 11/2010 | Dubois et al. | 351/177 |

* cited by examiner

*Primary Examiner* — Mohammed Hasan
(74) *Attorney, Agent, or Firm* — Carla Gannon Law

(57) ABSTRACT

An apparatus for and methods of determining that the placement and alignment of progressive add lenses (PALs) in a subject's frame are correct. Namely, a PAL verification tool includes a chart and light source, wherein the chart is viewed by the subject and the light source is worn by the subject during a PAL verification process. The PAL verification method may include the steps of positioning the subject with respect to a near fixation point, the subject viewing the near fixation point with one eye and bringing it into best and clearest vision, measuring and recording a first head position with respect to the near fixation point, the subject viewing the near fixation point with the other eye and bringing it into best and clearest vision, measuring and logging a second head position with respect to the near fixation point, and determining the amount and direction of the difference in the first and second head positions and correlating to an amount and direction of PAL misalignment. A measured misalignment exceeding certain tolerances indicates that a subject's PALs aren't properly positioned in their frame. A subject is suitable for correction if this misalignment causes the subject to experience visual or physical discomfort.

17 Claims, 11 Drawing Sheets

APPARATUS FOR AND METHODS OF DETERMINING IF PROGRESSIVE ADD LENSES (PALS) ARE PROPERLY POSITIONED IN A SUBJECT'S EYEGLASSES

FIELD OF THE DISCLOSURE

The present disclosure generally relates generally to progressive addition (or add) lenses and more particularly to an apparatus for and methods of verifying the correct placement of progressive add lenses (PALs) in eyeglass frames.

BACKGROUND

Progressive add lenses (PALs) are used to provide vision correction for near vision issues, such as presbyopia. Progressive add lenses are designed to have distance, near, and intermediate viewing zones. The intermediate zone joins the near and distance zones in a cosmetically acceptable way, such that no discontinuities in the lens are visible to people observing the wearer. PALs also provide the wearer with vision correction at multiple distances without the need for multiple breaks in the lens or multiple pairs of glasses.

However, in a significant percent of PAL wearers, the optical (pupillary) axis measurement commonly used by the optical industry produces an incorrect segment separation because the optical (pupillary) axis of the eye is not always the same as the visual axis of the eye. This biometric issue is called angle Kappa. The visual axis is one's line of vision, which is a straight line that joins the fovea of the eye with a fixation point. A consequence of using the optical (pupillary) axis measurement only for determining the placement of PAL viewing zones within eyeglass lenses is that the placement of the PAL viewing zones while aligning with the optical (pupillary) axes may not properly align with the patient's visual axes and, thus, the patient may experience blurriness and various forms of visual and physical discomfort, due to the subject's degraded binocular vision. In particular, the viewing areas of progressive lenses are narrow and, thus, any slight misalignment is disruptive to binocular vision. As a result, the patient is dissatisfied with his/her PAL eyeglasses and further time and money is spent for return visits to the eye care provider for follow-up corrective action. For these reasons, a need exists for new approaches for determining and/or verifying the accurate placement of PALs in a subject's eyeglass frames.

There are many negative factors with a PAL prescription that can cause a patient to experience visual or physical discomfort. These issues can include wrong segment height, PAL style, frame fitting issues, an incorrect prescription, and/or horizontal misalignment. These negative factors need to be discovered and corrected for the PAL wearer to have glasses that function correctly and comfortably. The optical industry has equipment and techniques for determining, verifying and correcting all these factors in a PAL prescription, except there is currently no apparatus or method for validating and correcting the horizontal visual axes alignment. Thus there is a need in the art for an apparatus and method that fills this void in the validation and correction process of this alignment issue.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

The presently disclosed subject matter provides an apparatus for and methods of verifying the correct placement of progressive add lenses (PALs) in eyeglass frames. Further, when the placement or alignment of the PALs is incorrect, the presently disclosed methods can be used to determine the exact linear error of the misalignment so that replacement PAL lenses can be manufactured without the error. The presently disclosed apparatus is a PAL verification tool that includes a chart having a linear measuring scale and a pin point light source to be attached to patient's eyeglasses or head, wherein the light source is directed at the measuring scale of the chart. The chart and the light source are used to indicate any misalignment of the PALs with respect to the patient's visual axes based, for example, on the side-to-side movement of either the patient's head or of the chart when checking the PAL alignment of one eye versus the PAL alignment of the other eye.

In various embodiments, the presently disclosed apparatus and methods enable an eye care professional to obtain accurate quantifiable data about the positions of PALs installed in a subject's eyeglasses and how they relate to a patient's visual axes. Further, this data enables an eye care professional to make adjustments to the PALs in relation to either fabrication, installation, or both, if necessary, for proper vision correction of the patient. Further, the terms "subject" and "patient" are used interchangeably herein.

Figure 1:
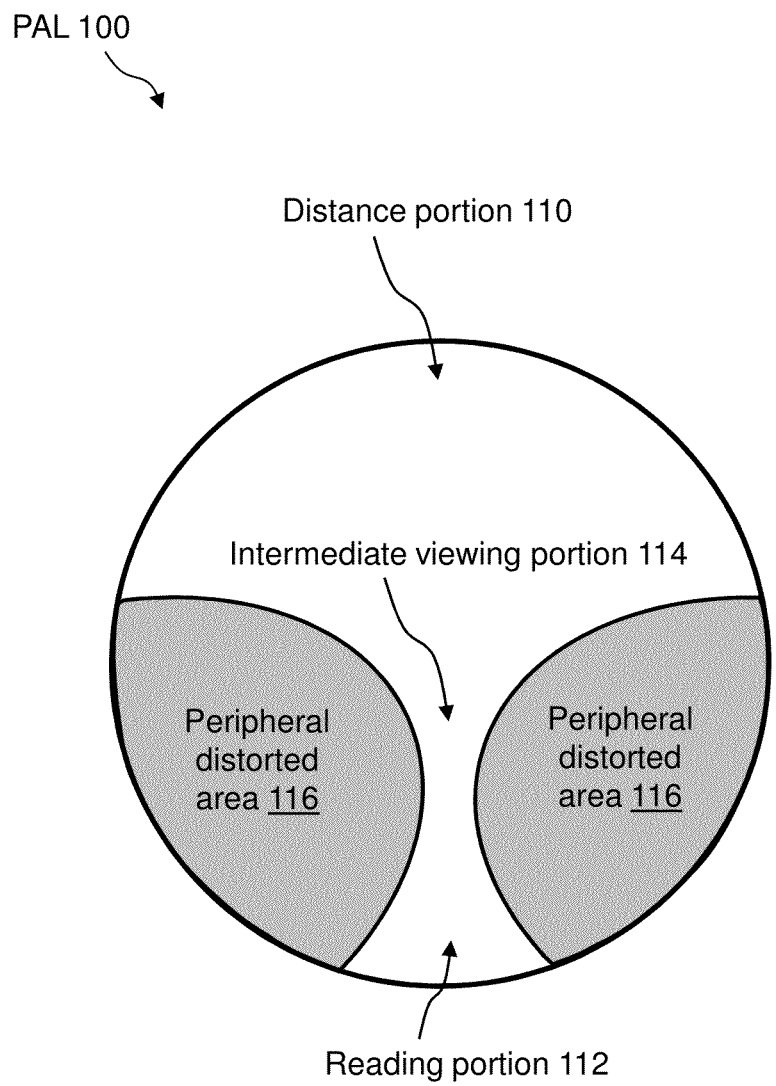
FIG. 1 illustrates a plan view of an example of a progressive add lens.

FIG. 1 illustrates a plan view of an example of a progressive add lens (PAL) 100. For example, PAL 100 includes a distance portion 110 and a reading portion 112 having an intermediate viewing portion 114 arranged therebetween. On either sides of intermediate viewing portion 114 are two peripheral distorted areas 116. For example, distance portion 110 in the upper region of the PAL 100 is the portion of the lens that is used for distance or far viewing. Further, reading portion 112 in the lower region of the PAL 100 is the portion of the lens that is used for close up or near viewing. Intermediate viewing portion 114 is the narrow region connecting distance portion 110 and reading portion 112, wherein intermediate viewing portion 114 provides the focus transition between distance portion 110 and reading portion 112. At it narrowest portion, the width of intermediate viewing portion 114 can be, for example, up to about 6 mm. In a set of eyeglasses there is a left PAL 100 and a right PAL 100. The prescription or correction characteristics of the left and right PALs 100 are unique to the user or subject whose vision is being corrected. The prescription or correction characteristics of the left and right PALs 100 may be the same or may be different. The right PAL 100 is hereafter called PAL 100R. The left PAL 100 is hereafter called PAL 100L. An example of a pair of PALs 100 installed in a set of eyeglasses is shown with reference to FIG. 3.

Figure 2:
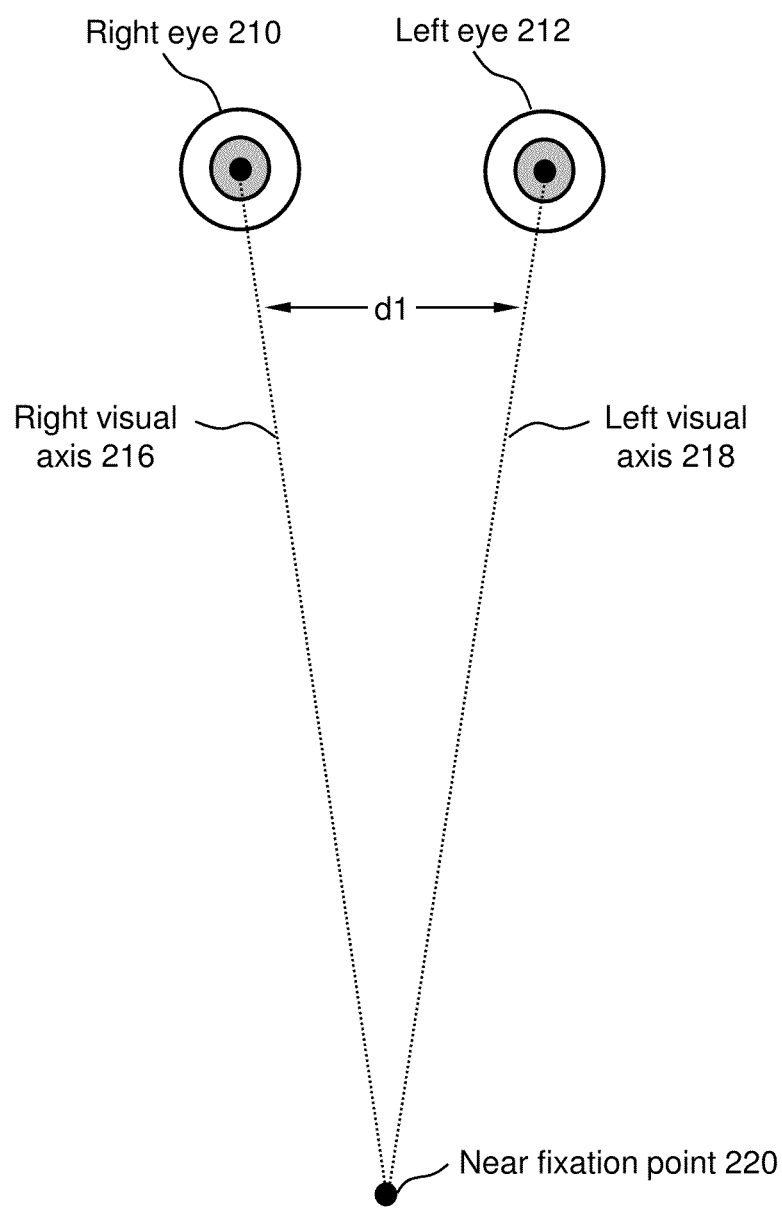
FIG. 2 through FIG. 6 show the relationship between the visual axes when the subject is viewing a near fixation point and the intermediate viewing portions of the subject's PALs.

FIG. 2 shows the visual axes of the subject's eyes, wherein the two visual axes converge at a near fixation point. Namely, FIG. 2 shows a right eye 210 and a left eye 212, which are the eyes of the subject of the presently disclosed PAL verification method. Associated with right eye 210 is the subject's right visual axis 216. Associated with left eye 212 is the subject's left visual axis 218. The visual axis is one's line of vision, which is a straight line that joins the fovea of the eye with the eye's fixation point. Namely, the subject's right visual axis 216 and left visual axis 218 converge at a near fixation point 220, wherein near fixation point 220 is most commonly about 16 inches (or about 40 cm) away from the subject. With respect to the presently disclosed methods, there is a distance d1 between right visual axis 216 and left visual axis 218, wherein the distance d1 is at the point or plane at which the subject's right visual axis 216 and left visual axis 218 pass through the PALs 100 in his/her eyeglasses (see FIG. 4).

Figure 3:
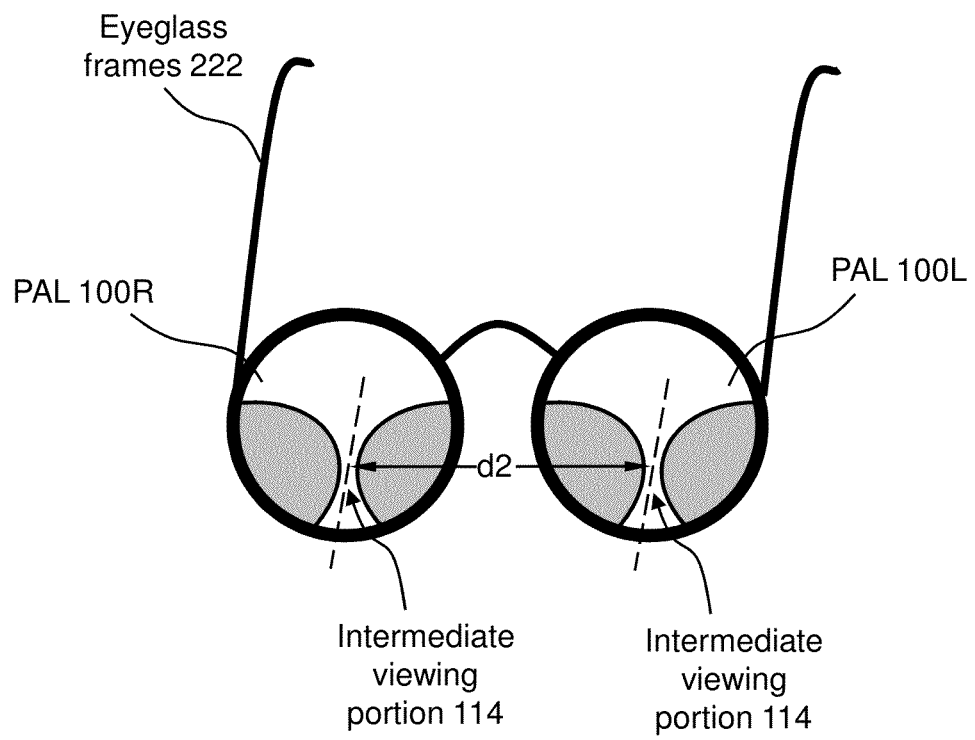

FIG. 3 shows a distance d2 between the respective intermediate viewing portions 114 of PAL 100R and PAL 100L installed a set of eyeglasses. Namely, FIG. 3 shows PAL 100R and PAL 100L installed in eyeglass frames 222. In this example, the distance d2 is the distance between the intermediate viewing portion 114 of PAL 100R and the intermediate viewing portion 114 of PAL 100L.

Figure 4:
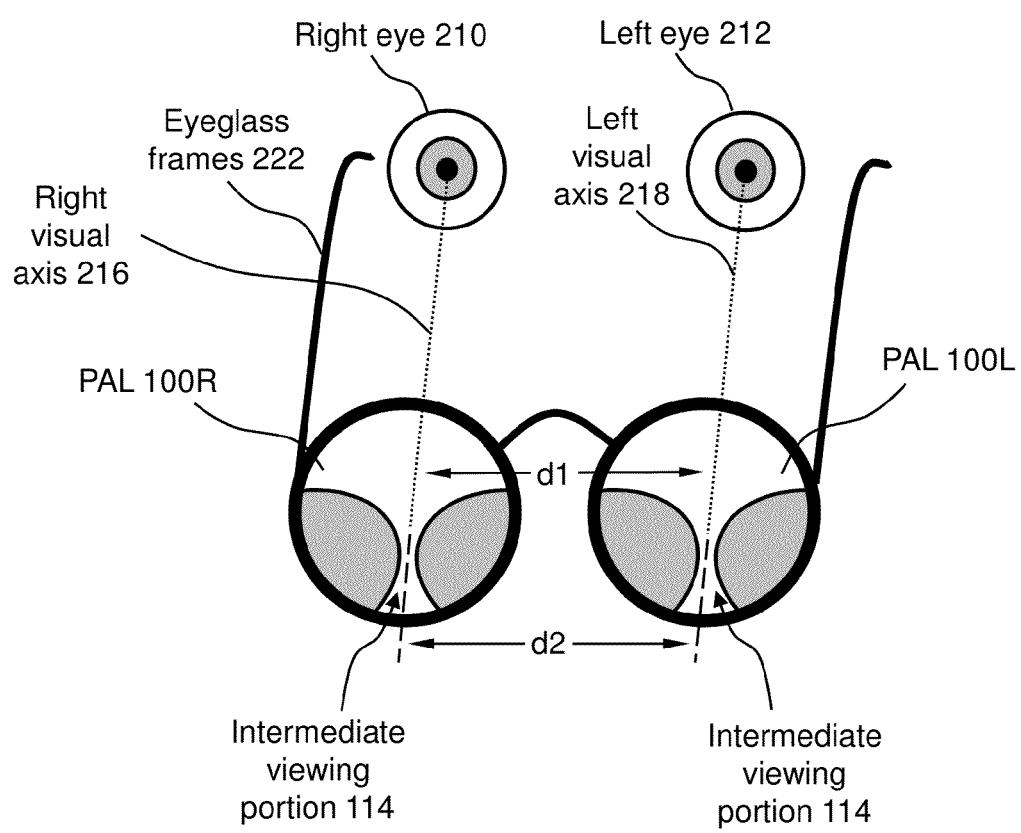

FIG. 4 illustrates a perspective view (not to scale) of an example of a visual alignment scenario 400. Namely, FIG. 4 shows the subject's right visual axis 216 and left visual axis 218 in relation to the two intermediate viewing portions 114 of PAL 100R and PAL 100L installed in eyeglass frames 222. In this example, at the point at which right visual axis 216 and left visual axis 218 pass through PALs 100, the distance d1 is substantially the same as distance d2, which is the desired outcome when making eyeglasses that include PALs, such as PAL 100R and PAL 100L. In other words, when distance d2 is substantially the same as distance d1, the PALs are fabricated properly and the subject's vision is properly corrected. By contrast, FIG. 5 and FIG. 6 describe scenarios in which distance d2 is not substantially the same as distance d1.

When a patient complains of visual or physical discomfort, such as blurred vision, double vision, reading area too narrow, struggling to find clear area, headache, fatigue, etc. while wearing their PAL prescription, it is necessary to determine the source of the problem. The apparatus and methods of the present invention determine whether d1 and d2 are aligned or not properly aligned.

If the alignment device determines that the subject's visual axes d1 are aligned with the subject's PAL optical centers d2, then the alignment device has determined that the factor of alignment is not an issue or cause of the subject's visual or physical discomfort and will attend to other factors as a cause for their discomfort.

If the alignment device determines that the d1 and d2 are not aligned, the alignment device can determine the exact amount of misalignment of between approximately 0.10 mm and up to 10.0 mm and use this information to correct this error on the new PAL RX.

The human negative response and tolerance to these errors range from none, where the patient suppresses the image in one eye, to extreme discomfort and total rejection of the PAL prescription, due to intolerance to any stereoscopic disruption. Thus it is important that any negative feedback by the patient is addressed by evaluating all factors of a PAL prescription.

Based on what the eye care professional has established with respect to patient feedback and measured d1 and d2 misalignment, a new set of PAL lenses, incorporating the correct alignment, can be crafted. It is expected that these new lenses will result in good vision and comfort for the PAL user.

Figure 5:
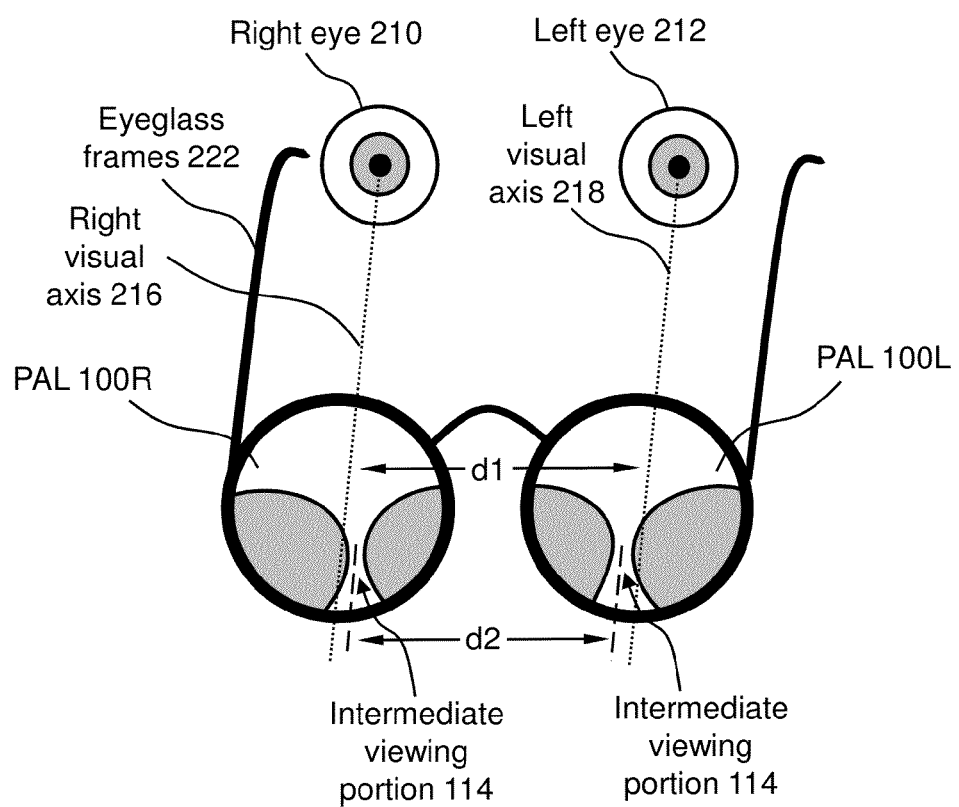

FIG. 5 illustrates a perspective view (not to scale) of an example of a visual alignment scenario 500. In this scenario, at the point at which right visual axis 216 and left visual axis 218 pass through PALs 100, the distance d2 between the intermediate viewing portions 114 of PAL 100R and PAL 100L is narrower than the distance d1 between the subject's right visual axis 216 and left visual axis 218. Because distance d2 is not substantially the same as distance d1, the subject's near binocular vision will be impaired. Consequently, the subject will be dissatisfied with his/her PALs and will likely make a return visit to his/her eye care professional.

Figure 6:
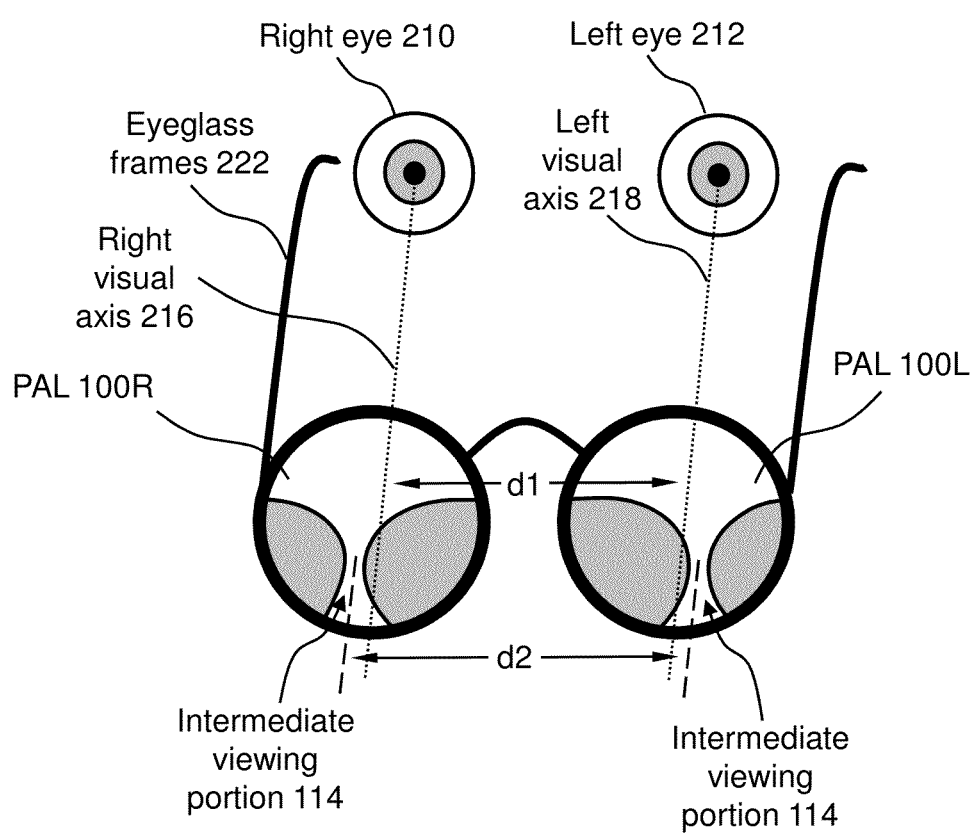

FIG. 6 illustrates a perspective view (not to scale) of another example of a visual alignment scenario 600. In this scenario, at the point at which right visual axis 216 and left visual axis 218 pass through the PALs 100, the distance d2 between the intermediate viewing portions 114 of PAL 100R and PAL 100L is longer than the distance d1 between the subject's right visual axis 216 and left visual axis 218. Again, because distance d2 is not substantially the same as distance d1, the subject's near binocular vision will be impaired. Consequently, the subject will be dissatisfied with his/her PALs and will likely make a return visit to his/her eye care professional.

Figure 7:
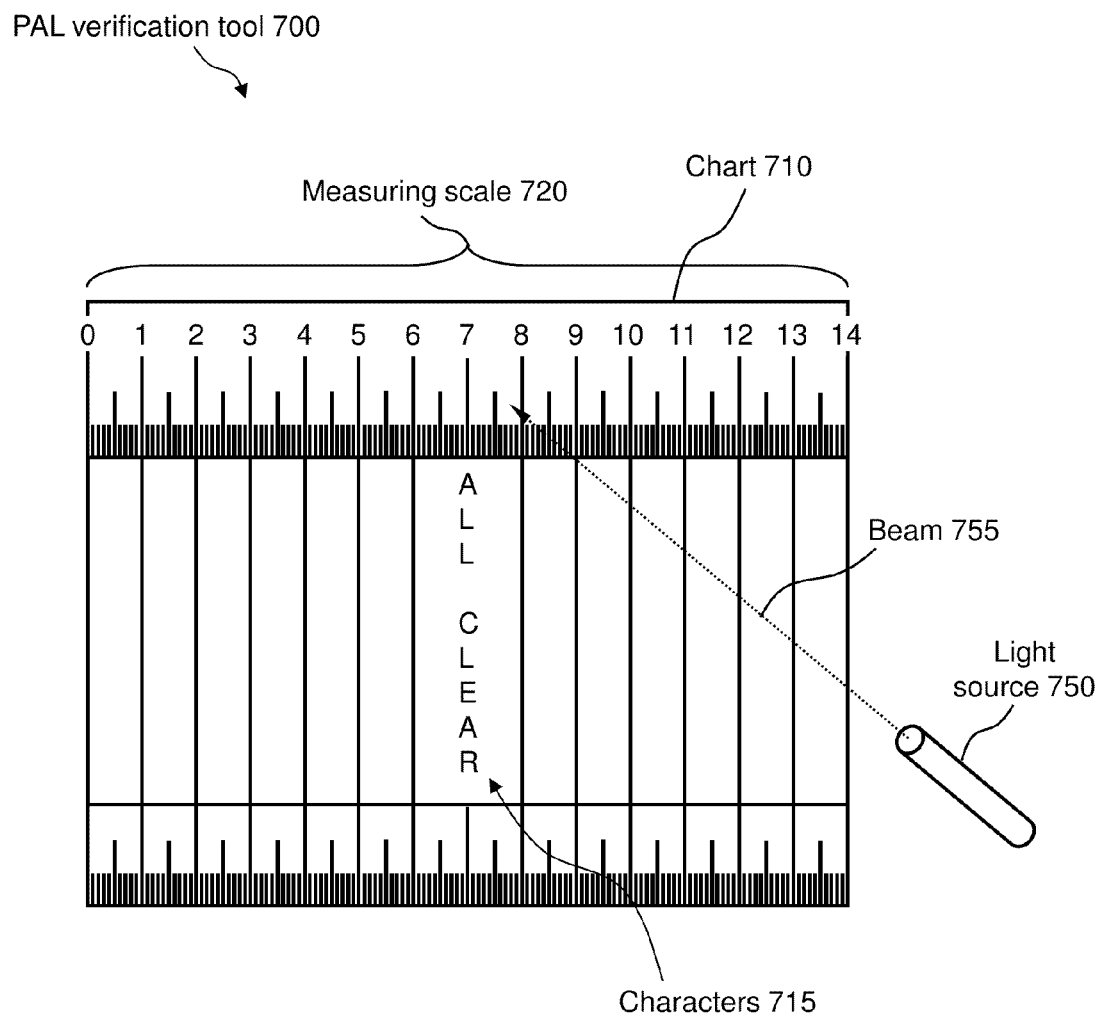
FIG. 7 shows an example of the presently disclosed PAL verification tool that includes a chart and light source.

FIG. 7 shows an example of a PAL verification tool 700 that includes a chart 710 and a pin point light source 750 that emits a beam 755, wherein chart 710 is viewed by the subject and light source 750 is worn by the subject during the presently disclosed PAL verification process. Chart 710 can be, for example, a paper, cardboard, plastic, or wooden chart. Chart 710 has certain characters 715 and a measuring scale 720 marked thereon. Characters 715 can be, for example, any alphanumeric characters on which the subject of the PAL verification process can focus. Measuring scale 720 can be any type of linear measuring scale. In one example, measuring scale 720 is a standard English ruler. In another example, measuring scale 720 is a standard metric ruler. In another example, measuring scale 720 is a custom linear measuring scale that is unitless. In one example, light source 750 is a laser source and therefore beam 755 is a visible laser beam. An example of a laser source is a standard laser pointer. In the example chart 710 shown in FIG. 7, from left to right, a number line progresses from the number "0" to the number "14," wherein the number "7" is at about the center of measuring scale 720. However, this is exemplary only. Measuring scale 720 can be numbered in any fashion. In the example chart 710 shown in FIG. 7, characters 715 are substantially aligned with the number "7" along measuring scale 720.

Each whole unit of measuring scale 720 can be correlated to a certain incremental distance along distance d2 between PAL 100R and PAL 100L when the chart 710 is viewed at a certain distance away from the subject's eye. The formula used to obtain this distance d2 at the PAL lens plane uses a ratio of 1 to 20 based on the PAL lens plane being 20 mm from the eye and chart 710 being 400 mm (16 inches) from the eye. In one example, each whole unit of measuring scale 720 is a 1-cm (10 mm) unit that correlates to a ½-mm increment along distance d2 between PAL 100R and PAL 100L when the chart 710 is viewed at about 16 inches (or about 40 cm) away from the subject's eyes. In yet another example which is not shown, each whole unit of measuring scale correlates to a ½-mm increment along distance d2 between PAL 100R and PAL 100L when the chart 710 is viewed at about 16 inches (or about 40 cm) away from the subject's eye.

Figure 8:
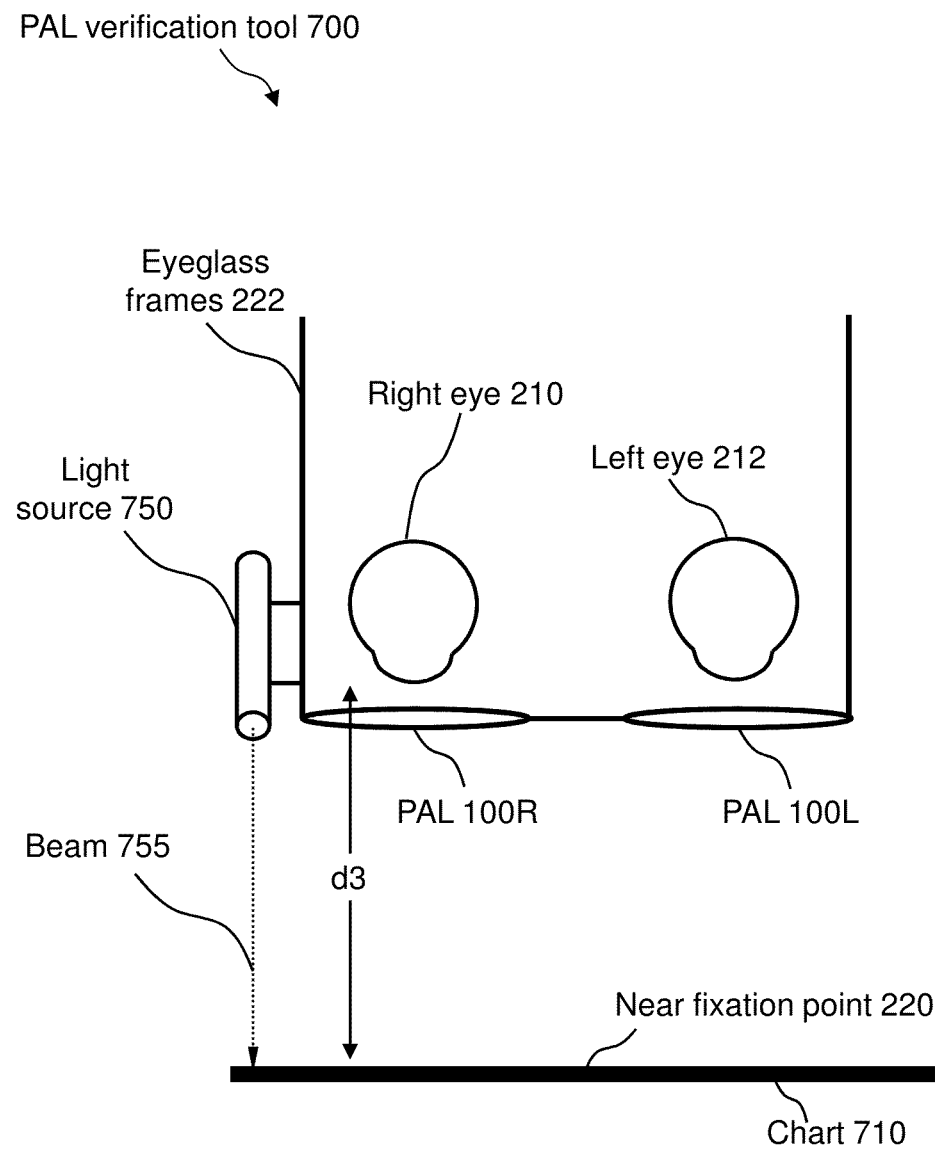
FIG. 8 illustrates a top down view of an example of the PAL verification tool when in use.

FIG. 8 illustrates (not to scale) a top down view of an example of PAL verification tool 700 when in use. In this example, the subject who is wearing the eyeglass frames 222 in which PAL 100R and PAL 100L are installed is facing chart 710. Further, light source 750 is affixed to eyeglass frames 222 and aimed at chart 710 so that beam 755 impinges on measuring scale 720 of chart 710. Light source 750 can be affixed to any portion of eyeglass frames 222 using, for example, a plastic or metal clip. The destination focal point of beam 755 is directed or aimed at measuring scale 720 on chart 710. In other embodiments, light source 750 is not affixed to eyeglass frames 222. Instead, light source 750 is mounted on a stretchable headband and worn around the subject's head. Light source 750 can be implemented in any manner that allows beam 755 to be aimed at chart 710 and to move in concert with any movement of the subject's head.

Further, chart 710 is set a certain distance d3 away from the subject's eyes, wherein the distance d3 correlates to the distance away of the near fixation point 220 shown in FIG. 2. In one example, the distance d3 is about 16 inches (or about 40 cm). Again, the chart 710 is designed such that the units of measuring scale 720 have a certain correlation to the increments along distance d2 between PAL 100R and PAL 100L when the chart 710 is placed a certain distance d3 from the subject's eyes. In one example, when the distance d3 is set at 16 inches, a 1-cm unit of measuring scale 720 correlates to a ½-mm increment along distance d2 between PAL 100R and PAL 100L.

Figure 9:
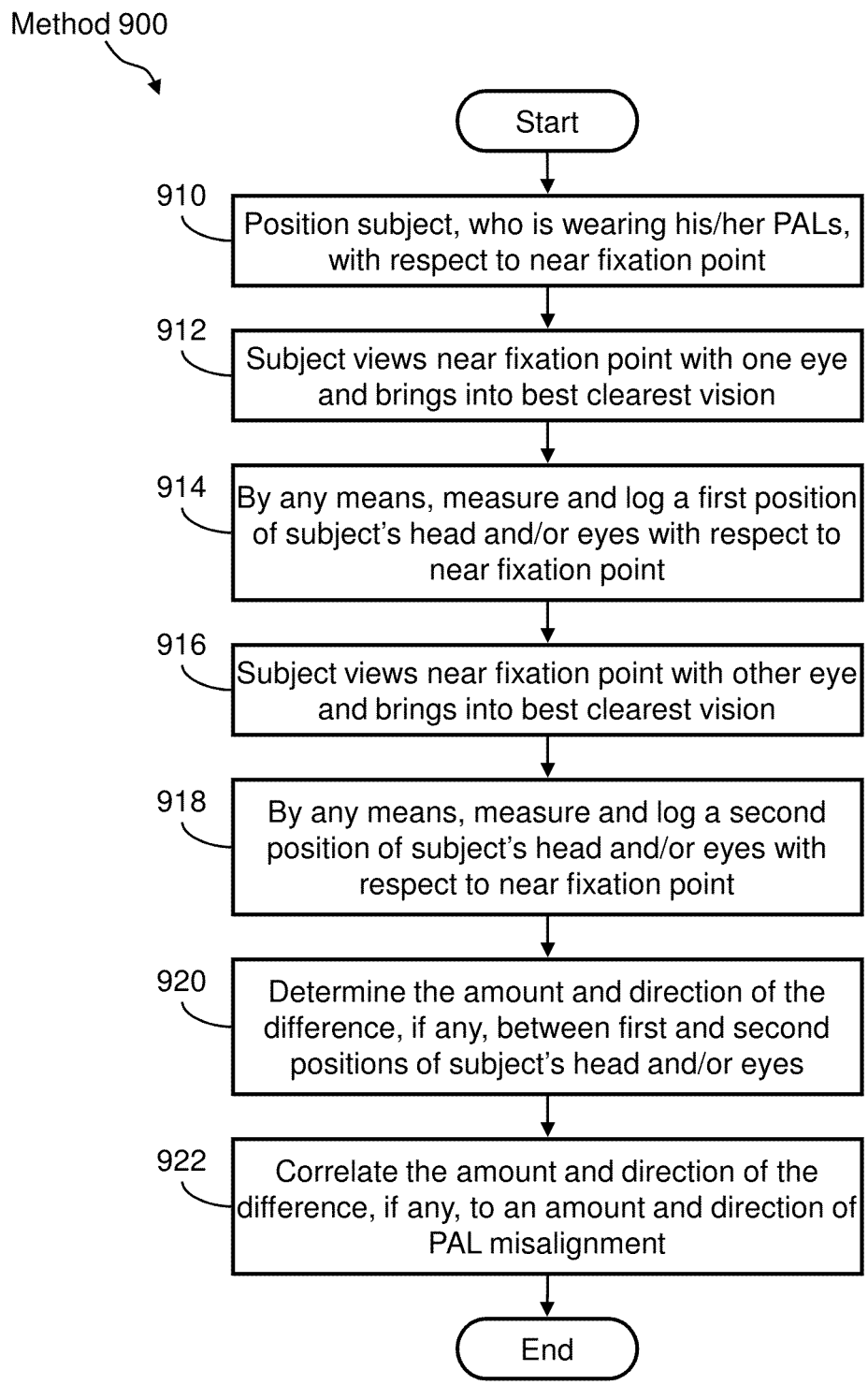
FIG. 9 illustrates an example of a flow diagram of a method of performing a PAL verification process using the presently disclosed PAL verification tool according to a minimum configuration.

FIG. 9 illustrates an example of flow diagram of a method 900 of performing a PAL verification process using the presently disclosed PAL verification tool 700 according to a minimum configuration. Method 900 includes, but is not limited to, the following steps. At a step 910, with the subject of the PAL verification process wearing his/her eyeglass frames 222 having PALs 100, the subject is positioned with respect to a near fixation point 220. In one example, the subject is positioned a certain distance d3 with respect to the chart 710. For example, the subject is positioned such that the distance d3 between the PALs 100 and chart 710 is about 16 inches (or 40 cm), whereas 16 inches (or 40 cm) allows a 1-cm unit of measuring scale 720 to correlate to a ½-mm increment of distance d2 between PAL 100R and PAL 100L. The method 900 is not limited to using the chart 710 only as the near fixation point 220. This is exemplary only. The method 900 can use any physical, virtual, or electronic object or image as the near fixation point 220. For example, optical and/or electronic equipment can be provided that allows the subject to rest his/her chin in a holder while viewing a near fixation point 220 that is provided optically or electronically.

At a step 912, the subject of the PAL verification process views the near fixation point 220 (e.g., the chart 710) with one eye while covering the other eye and brings the near fixation point 220 into best and clearest vision. In one example, the subject views the chart 710 with his/her right eye while covering the left eye. In another example, the subject views the chart 710 with his/her left eye while covering the right eye. In either case, the subject is instructed to adjust side-to-side the position of his/her head until, for example, the characters 715 of the chart 710 are in best and clearest vision. In one example, this can be done by holding the chart 710 stationary and allowing the subject to move his/her head side-to-side. In another example, this can be done by holding the subject's head stationary and moving the chart 710 side-to-side. In yet another example, this can be done using optical and/or electronic equipment that allows the subject to view a near fixation point 220 and bring it into best and clearest vision.

At a step 914, by any means, the eye care professional measures and records the position of subject's head and/or eyes with respect to the near fixation point 220. In one example, the eye care professional uses the light source 750 in combination with the chart 710 as shown and described in FIG. 7 and FIG. 8. In this example, the light source 750 impinges on the measuring scale 720 and the eye care professional logs the number at the point of impingement. In another example, optical and/or electronic equipment is used that provides this measurement.

At a step 916, the subject of the PAL verification process views the near fixation point 220 (e.g., the chart 710) with the other eye and brings the near fixation point 220 into best and clearest vision. In one example, if the subject started with his/her right eye in the step 910, then the subject now covers his/her right eye and views the chart 710 with the left eye. In another example, if the subject started with his/her left eye in the step 910, then the subject now covers his/her left eye and views the chart 710 with the right eye. In either case, the subject is instructed to adjust side-to-side the position of his/her head until, for example, characters 715 of the chart 710 are in best and clearest vision. In one example, this can be done by holding the chart 710 stationary and the subject moving his/her head side-to-side. In another example, this can be done by holding the subject's head stationary and moving the chart 710 side-to-side. In yet another example, this can be done using optical and/or electronic equipment that allows the subject to view a near fixation point 220 and bring it into best and clearest vision.

At a step 918, by any means, the eye care professional measures and logs the position of subject's head and/or eyes with respect to the near fixation point 220. In one example, the eye care professional uses the light source 750 in combination with the chart 710 as shown and described in FIG. 7 and FIG. 8. In this example, the light source 750 impinges on the measuring scale 720 and the eye care professional logs the number at the point of impingement. In another example, optical and/or electronic equipment is used that provides this measurement.

At a step 920, the amount and direction of the difference, if any, in the position of subject's head from viewing the near fixation point 220 with one eye in step 912 versus the other eye in step 916 is determined. In one example, this can be determined by calculating the difference, if any, in the numbers that are logged in steps 914 and 918 and also determining the direction of movement (e.g., positive or negative direction along the measuring scale 720). In another example, optical and/or electronic equipment is used to determine the amount and direction of the difference, if any.

At a step 922, the amount and direction of the difference determined in step 920, if any, is correlated to an amount and direction of the PAL misalignment. In one example, the amount and direction of the difference correlates to the distance d2 between PAL 100R and PAL 100L being too narrow with respect to the distance d1 between the subject's right visual axis 216 and left visual axis 218. In another example, the amount and direction of the difference correlates to the distance d2 between PAL 100R and PAL 100L being too wide with respect to the distance d1 between the subject's right visual axis 216 and left visual axis 218.

More details of specific examples of implementing the method 900 using PAL verification tool 700 (i.e., chart 710 and light source 750) are shown and described herein below with reference to FIG. 10 and FIG. 11.

Figure 10:
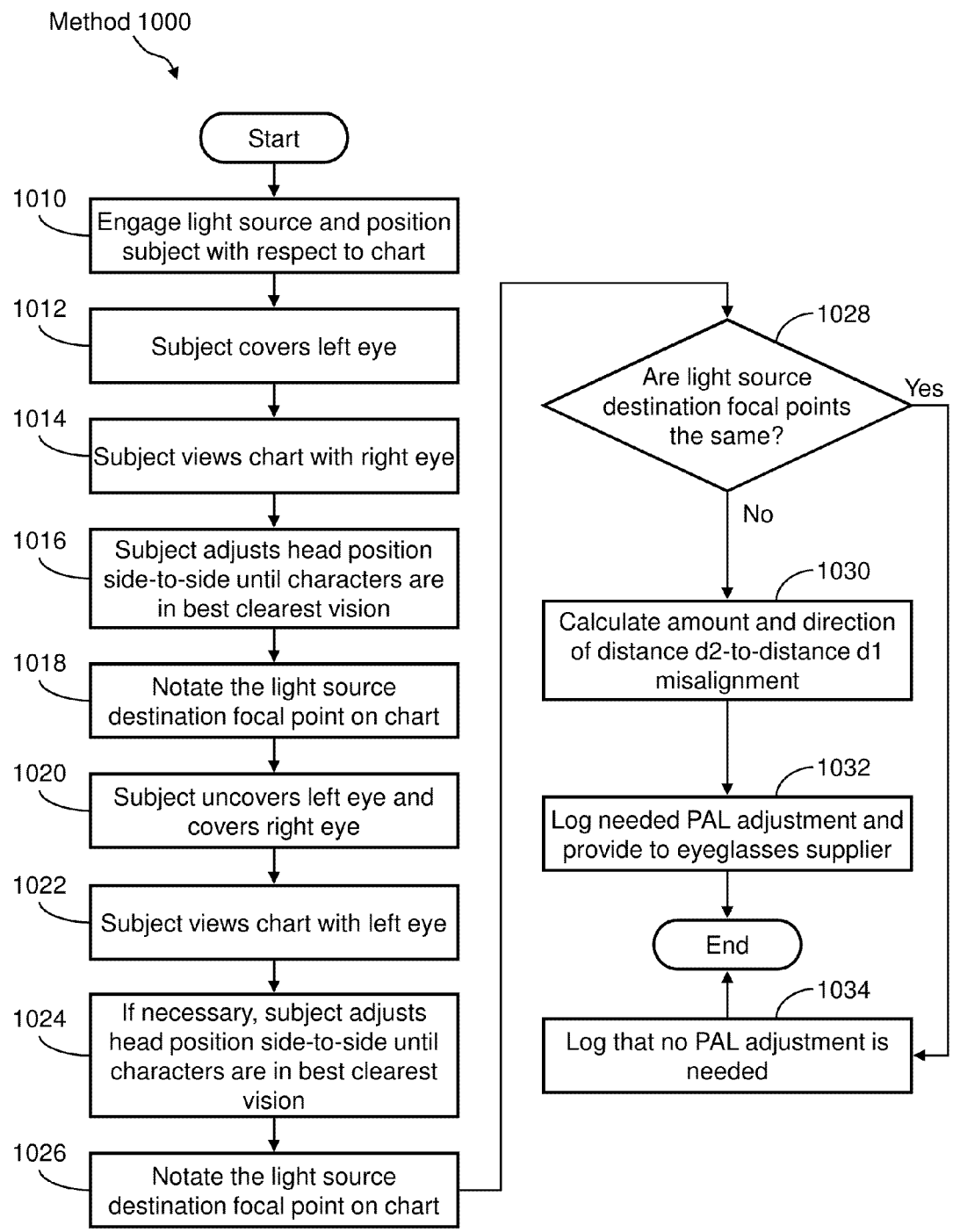
FIG. 10 illustrates an example of a flow diagram of a method of performing a PAL verification process using the presently disclosed PAL verification tool and starting with the subject's right eye.

FIG. 10 illustrates an example of flow diagram of a method 1000 of performing a PAL verification process using the presently disclosed PAL verification tool 700 and starting with the subject's right eye. Method 1000 includes, but is not limited to, the following steps.

At a step 1010, with the subject of the PAL verification process wearing his/her eyeglass frames 222 having PALs 100, light source 750 is affixed to the subject and the subject is positioned with respect to chart 710. In one example, using a plastic or metal clip, light source 750 is affixed to the right bow of eyeglass frames 222 (see FIG. 8) that are being worn by the subject. In another example, light source 750 is mounted on a stretchable headband and worn around the subject's head. Then, the subject of the PAL verification process is positioned with respect to chart 710. In one example, the subject is positioned such that the distance d3 between the PALs 100 and chart 710 is about 16 inches (or 40 cm), whereas 16 inches (or 40 cm) allows a 1-cm unit of measuring scale 720 to correlate to a ½-mm increment of distance d2 between PAL 100R and PAL 100L. Method 1000 proceeds to step 1012.

At a step 1012, the subject covers his/her left eye 212. For example, this may be done by the subject simply closing his/her left eye 212 or by using any industry standard instrument (e.g., a handheld paddle) to block the view of left eye 212. Method 1000 proceeds to step 1014.

At a step 1014, the subject views the chart 710 with his/her right eye 210. For example, the subject is instructed by the eye care professional conducting the PAL verification process to fix the gaze of his/her right eye 210 on characters 715 of chart 710. Method 1000 proceeds to step 1016.

At a step 1016, the subject adjusts their head side-to-side until the characters 715 of chart 710 are in best and clearest vision to the right eye 210. For example, the subject is instructed by the eye care professional to move his/her head side-to-side to a position in which the letters, numbers, or words in characters 715 of chart 710 are most clear and able to be read by the subject and relayed verbally to the eye care professional. In so doing, the subject aligns the right visual axis 216 of his/her right eye 210 with intermediate viewing portion 114 of PAL 100R. At the same time that the subject is reading characters 715 of chart 710 with his/her right eye 210, beam 755 of light source 750 is impinging on measuring scale 720 of chart 710. In other embodiments, instead of the subject moving his/her head, the subject's head is held stationary while the position of the chart 710 is adjusted side-to-side to bring the characters 715 of chart 710 into best and clearest vision. Method 1000 proceeds to step 1018.

At a step 1018, the eye care professional notates the destination focal point of beam 755 of light source 750 on measuring scale 720 of chart 710. For example, for the subject's right eye 210, the eye care professional notates the number indicated at the location where beam 755 intersects with measuring scale 720 of chart 710. The number noted in this step is hereafter called VALUE1. VALUE1 is, for example, 7.2, 8.7, or 9.1. Method 1000 proceeds to step 1020.

At step 1020, the subject uncovers their left eye 212 and covers right eye 210. For example, the subject opens his/her left eye 212 or removes the instrument that was blocking his/her left eye 212. Then, the subject covers his/her right eye 210. For example, this may be done by the subject simply closing his/her right eye 210 or by using any industry standard instrument to block the view of right eye 210. Method 1000 proceeds to step 1022.

At a step 1022, the subject views the chart 710 with his/her left eye 212. For example, the subject is instructed by the eye care professional conducting the PAL verification process to fix the gaze of his/her left eye 212 on characters 715 of chart 710. Method 1000 proceeds to step 1024.

At a step 1024, the subject adjusts their head position side-to-side until the characters 715 of chart 710 are in best and clearest vision to the left eye 212. For example, the subject is instructed by the eye care professional to move his/her head side-to-side to a position in which the letters, numbers, or words in characters 715 of chart 710 are most clear and able to be read by the subject and relayed verbally to the eye care professional. In so doing, the subject aligns the left visual axis 218 of his/her left eye 212 with the viewing portion 114 of PAL 100L. At the same time that the subject is reading characters 715 of chart 710 with his/her left eye 212, beam 755 of light source 750 is impinging on measuring scale 720 of chart 710. In other embodiments, instead of the subject moving his/her head, the subject's head is held stationary while the position of the chart 710 is adjusted side-to-side to bring the characters 715 of chart 710 into best and clearest vision. Method 1000 proceeds to step 1026.

At a step 1026, the eye care professional notates the destination focal point of beam 755 of light source 750 on measuring scale 720 of chart 710. For example, for the subject's left eye 212, the eye care professional notates the number indicated at the location where beam 755 intersects with measuring scale 720 of chart 710. The number noted in this step is hereafter called VALUE2. VALUE2 is, for example, 6.6, 9.2, or 11.5. Method 1000 proceeds to decision step 1028.

At a decision step 1028, it is determined whether the destination focal points of light source 750 on chart 710 for right eye 210 (VALUE1 from step 1018) and left eye 212 (VALUE2 from step 1026) are the same. For example, the eye care professional compares VALUE1 from step 1018 with VALUE2 from step 1026 and determines whether they are the same or different. If VALUE1 from step 1018 is the same as VALUE2 from step 1026 (e.g., VALUE1=8.3 and VALUE2=8.3), then distance d2 is substantially the same as distance d1 and method 1000 proceeds to step 1034. However, if VALUE1 from step 1018 is not the same as VALUE2 from step 1026 (e.g., VALUE1=8.3 and VALUE2=6.9), then distance d2 is not the same as distance d1 method 1000 proceeds to step 1030.

At a step 1030, the amount and direction of the distance d2-to-distance d1 misalignment is calculated. First, the difference or delta between VALUE1 from step 1018 and VALUE2 from step 1026 is calculated. This determines the amount of misalignment between distance d2 and distance d1. Next, it is determined whether VALUE2 from step 1026 is greater than or less than VALUE1 from step 1018. This determines the direction of the misalignment between distance d2 and distance d1. Namely, whether the distance d2 is greater than the distance d1 (i.e., distance d2 is too wide) or less than the distance d1 (i.e., distance d2 is too narrow). Two examples of these calculations are given as follows.

Example 1

If VALUE1=8.1 and VALUE2=6.9, then delta=1.2, then VALUE2<VALUE1. Conclusion—the distance d2 is too narrow by 1.2 mm. Assuming that the subject is experiencing a negative reaction to the PAL prescription, the subject's eyeglasses need to be refabricated such that the distance d2 between PAL 100R and PAL 100L is 1.2 mm wider than the distance d2 of the current eyeglasses.

Example 2

If VALUE1=9.6 and VALUE2=12.1, then delta=2.5, then VALUE2>VALUE1. Conclusion—the distance d2 is too wide by 1.2 mm. Assuming that the subject is experiencing a negative reaction to the PAL prescription, the subject's eyeglasses need to be refabricated such that the distance d2 between PAL 100R and PAL 100L is 2.5 mm narrower than the distance d2 of the current eyeglasses. Method 1000 proceeds to step 1032.

At a step 1032, the eye care professional records the needed adjustment to PALs and provides adjustment data to the supplier/manufacturer of the subject's eyeglasses. Per Example 1 in step 1030, if the distance d2 between the intermediate viewing portions 114 of PAL 100R and PAL 100L needs to be increased by 1.2 mm, this information is provided to the supplier/manufacturer of the subject's eyeglasses so that this adjustment can be made. Per Example 2 in step 1030, if the distance d2 between the intermediate viewing portions 114 of PAL 100R and PAL 100L needs to be decreased by 2.5 mm, this information is provided to the supplier/manufacturer of the subject's eyeglasses so that this adjustment can be made. Method 1000 ends. At a step 1034, the eye care professional records that no adjustment is needed to the subject's PALs. Method 1000 ends.

Figure 11:
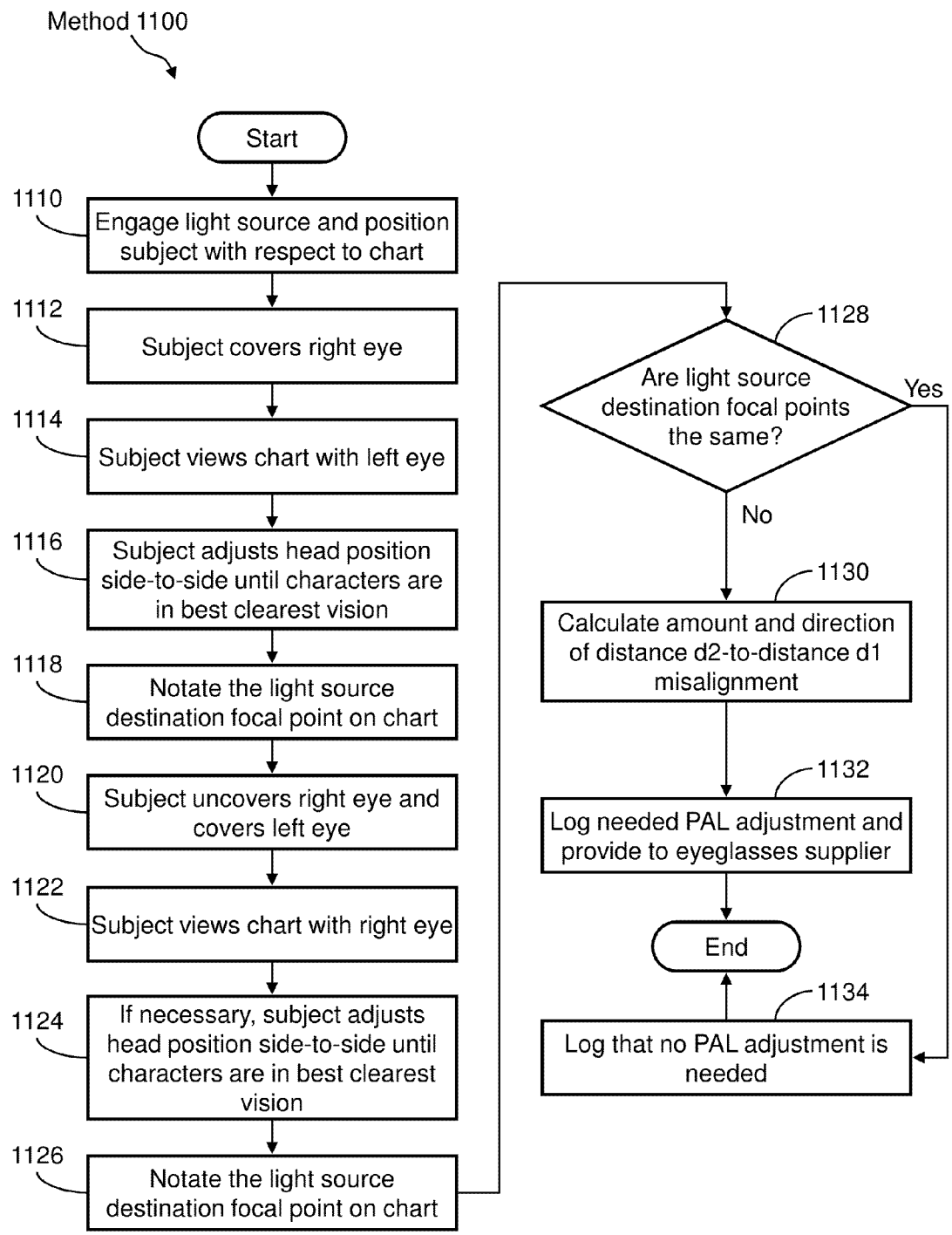
FIG. 11 illustrates an example of a flow diagram of a method of performing a PAL verification process using the presently disclosed PAL verification tool and starting with the subject's left eye.

FIG. 11 illustrates an example of flow diagram of a method 1100 of performing a PAL verification process using the presently disclosed PAL verification tool 700 and starting with the subject's left eye. Method 1100 includes, but is not limited to, the following steps:

At a step 1110, with the subject of the PAL verification process wearing his/her eyeglass frames 222 having PALs 100, light source 750 is affixed to the subject and the subject is positioned with respect to chart 710. In one example, using a plastic or metal clip, light source 750 is affixed to the right bow of eyeglass frames 222 (see FIG. 8) that are being worn by the subject. In another example, light source 750 is mounted on a stretchable headband and worn around the subject's head. Then, the subject of the PAL verification process is positioned with respect to chart 710. In one example, the subject is positioned such that the distance d3 between the PALs 100 and chart 710 is about 16 inches (or 40 cm), whereas 16 inches (or 40 cm) allows a 1-cm unit of measuring scale 720 to correlate to a ½-mm increment of distance d2 between PAL 100R and PAL 100L. Method 1100 proceeds to step 1112.

At a step 1112, the subject covers his/her right eye 210. For example, this may be done by the subject simply closing his/her right eye 210 or by using any industry standard instrument (e.g., a handheld paddle) to block the view of right eye 210. Method 1100 proceeds to step 1114.

At a step 1114, the subject views the chart 710 with his/her left eye 212. For example, the subject is instructed by the eye care professional conducting the PAL verification process to fix the gaze of his/her left eye 212 on characters 715 of chart 710. Method 1100 proceeds to step 1116.

At a step 1116, the subject adjusts their head position side-to-side until the characters 715 of chart 710 are in best and clearest vision to the left eye 212. For example, the subject is instructed by the eye care professional to move his/her head side-to-side to a position in which the letters, numbers, or words in characters 715 of chart 710 are most clear and able to be read by the subject and relayed verbally to the eye care professional. In so doing, the subject aligns the left visual axis 218 of his/her left eye 212 with intermediate viewing portion 114 of PAL 100L. At the same time that the subject is reading characters 715 of chart 710 with his/her left eye 212, beam 755 of light source 750 is impinging on measuring scale 720 of chart 710. In other embodiments, instead of the subject moving his/her head, the subject's head is held stationary while the position of the chart 710 is adjusted side-to-side to bring the characters 715 of chart 710 into best and clearest vision. Method 1100 proceeds to step 1118.

At a step 1118, the eye care professional notates the destination focal point of beam 755 of light source 750 on measuring scale 720 of chart 710. For example, for the subject's left eye 212, the eye care professional notates the number indicated at the location where beam 755 intersects with measuring scale 720 of chart 710. The number noted in this step is hereafter called VALUE1. VALUE1 is, for example, 7.2, 8.7, or 9.1. Method 1100 proceeds to step 1120.

At step 1120, the subject uncovers their right eye 210 and covers left eye 212. For example, the subject opens his/her right eye 210 or removes the instrument that was blocking his/her right eye 210. Then, the subject covers his/her left eye 212. For example, this may be done by the subject simply closing his/her left eye 212 or by using any industry standard instrument to block the view of left eye 212. Method 1100 proceeds to step 1122.

At a step 1122, the subject views the chart 710 with his/her right eye 210. For example, the subject is instructed by the eye care professional conducting the PAL verification process to fix the gaze of his/her right eye 210 on characters 715 of chart 710. Method 1100 proceeds to step 1124.

At a step 1124, the subject adjusts their head position side-to-side until the characters 715 of chart 710 are in best and clearest vision to the right eye 210. For example, the subject is instructed by the eye care professional to move his/her head side-to-side to a position in which the letters, numbers, or words in characters 715 of chart 710 are most clear and able to be read by the subject and relayed verbally to the eye care professional. In so doing, the subject aligns the right visual axis 216 of his/her right eye 210 with intermediate viewing portion 114 of PAL 100R. At the same time that the subject is reading characters 715 of chart 710 with his/her right eye 210, beam 755 of light source 750 is impinging on measuring scale 720 of chart 710. In other embodiments, instead of the subject moving his/her head, the subject's head is held stationary while the position of the chart 710 is adjusted side-to-side to bring the characters 715 of chart 710 into best and clearest vision. Method 1100 proceeds to step 1126.

At a step 1126, the eye care professional notates the destination focal point of beam 755 of light source 750 on measuring scale 720 of chart 710. For example, for the subject's right eye 210, the eye care professional notates the number indicated at the location where beam 755 intersects with measuring scale 720 of chart 710. The number noted in this step is hereafter called VALUE2. VALUE2 is, for example, 6.6, 9.2, or 11.5. Method 1100 proceeds to decision step 1128.

At a decision step 1128, it is determined whether the destination focal points of light source 750 on chart 710 for left eye 212 (VALUE1 from step 1118) and right eye 210 (VALUE2 from step 1126) are the same. For example, the eye care professional compares VALUE1 from step 1118 with VALUE2 from step 1126 and determines whether they are the same or different. If VALUE1 from step 1118 is the same as VALUE2 from step 1126 (e.g., VALUE1=8.3 and VALUE2=8.3), then distance d2 is the same as distance d1 and method 1100 proceeds to step 1134. However, if VALUE1 from step 1118 is not the same as VALUE2 from step 1126 (e.g., VALUE1=8.3 and VALUE2=6.9), then distance d2 is not the same as distance d1 and method 1100 proceeds to step 1130.

At a step 1130, the amount and direction of the distance d2-to-distance d1 misalignment is measured and calculated. First, the difference or delta between VALUE1 from step 1118 and VALUE2 from step 1126 is measured. This determines the amount of misalignment between distance d2 and distance d1. Next, it is determined whether VALUE2 from step 1126 is greater than or less than VALUE1 from step 1118. This determines the direction of the misalignment between distance d2 and distance d1. Namely, whether the distance d2 is greater than the distance d1 (i.e., distance d2 is too narrow) or less than the distance d1 (i.e., distance d2 is too wide). Two examples of these calculations are given as follows.

Example 1

If VALUE1=8.1 and VALUE2=6.9, then delta=1.2, then VALUE2<VALUE1. Conclusion—the distance d2 is too wide by 1.2 mm. The subject's eyeglasses need to be refabricated such that the distance d2 between PAL 100R and PAL 100L is 1.2 mm narrow than the distance d2 of the current eyeglasses.

Example 2

If VALUE1=9.6 and VALUE2=12.1, then delta=2.5, then VALUE2>VALUE1. Conclusion—the distance d2 is too narrow by 1.2 mm. The subject's eyeglasses need to be refabricated such that the distance d2 between PAL 100R and PAL 100L is 2.5 mm wider than the distance d2 of the current eyeglasses. Method 1100 proceeds to step 1132.

At a step 1132, the eye care professional records the needed adjustment to PALs and provides adjustment data to the supplier/manufacturer of the subject's eyeglasses. Per Example 1 in step 1130, if the distance d2 between the intermediate viewing portions 114 of PAL 100R and PAL 100L needs to be increased by 1.2 mm, this information is provided to the supplier/manufacturer of the subject's eyeglasses so that this adjustment can be made. Per Example 2 in step 1130, if the distance d2 between the intermediate viewing portions 114 of PAL 100R and PAL 100L needs to be decreased by 2.5 mm, this information is provided to the supplier/manufacturer of the subject's eyeglasses so that this adjustment can be made. Method 1100 ends.

At a step 1134, the eye care professional logs that no adjustment is needed to the subject's PALs. Method 1100 ends.

An exemplary embodiment has been disclosed above and illustrated in the accompanying drawings. Unless otherwise indicated or nonsensical, all ranges include stated endpoints as well as all increments there between, and "approximately" and the like mean+/−10%. It will be understood by those skilled in the art that various changes, omissions and additions may be made to that which is specifically disclosed herein without departing from the spirit and scope of the present invention. By way of example, this invention would be suitable with any style of eye glass frame, with subsequent lens repositioning relative to focal points.

I claim:

1. An apparatus for determining correct placement of PALS in a subject's eyeglass frames comprising:
   a. A chart including a measuring scale having a plurality of marked increments oriented horizontally, said increments including a left endpoint and a right endpoint;
   b. At least one distinguishable character on said chart, said character positioned approximately equidistant from said left endpoint and said right endpoint; and
   c. A light source positioned in front of said chart, said light source emitting a beam that converges with said chart.

2. The apparatus of claim 1 wherein said increments are labeled numerically.

3. The apparatus of claim 1 wherein said at least one distinguishable character is a plurality of characters positioned vertically.

4. The apparatus of claim 1 wherein said chart is adjustable side-to-side.

5. The apparatus of claim 1 wherein said light source is releasably connected to said subject.

6. The apparatus of claim 5 wherein said light source is releasably connected to said subject's eyeglasses.

7. A method for determining if progressive add lenses are properly positioned in a subject's eyeglasses comprising the steps of:
   a. Fitting a subject with eyeglasses having progressive add lenses;
   b. Positioning said subject in front of a chart having characters;
   c. Obscuring vision in said subject's second eye;
   d. Adjusting position of said subject relative to said chart by side-to-side motion;
   e. Ceasing side-to-side motion at a first position where said characters are most clearly distinguished by said subject's first eye;
   f. Recording said first position;
   g. Obscuring vision in said subject's first eye;
   h. Adjusting position of said subject relative to said chart by side-to-side motion;
   i. Ceasing side-to-side motion at a second position where said characters are most clearly distinguished by said subject's second eye;
   j. Recording said second position; and
   k. Positioning said progressive add lenses within a pair of eyeglasses based on comparison of first and second positions.

8. The method of claim 7 further including the preceding step of selecting a subject who has experienced symptoms of improper alignment.

9. The method of claim 7 wherein said steps of adjusting position of said subject relative to said chart by side-to-side motion includes moving position of said subject but keeping said chart stationary.

10. The method of claim 7 wherein said steps of adjusting position of said subject relative to said chart by side-to-side motion includes moving position of said chart but keeping said subject stationary.

11. The method of claim 7 further including the preceding steps of releasably connecting a light source to said subject, and directing said light source's beam towards said chart.

12. The method of claim 11 wherein said step of recording said first position includes recording position of said beam's convergence with chart.

13. The method of claim 12 wherein said step of recording said second position includes recording position of said beam's convergence with chart.

14. The method of claim 7 wherein said step of positioning said progressive add lenses within a pair of eyeglasses includes positioning said progressive add lenses within said eyeglasses.

15. A method for adjusting progressive add lenses in a subject's eyeglasses comprising the steps of:

a. Selecting a subject who has experienced symptoms of improper alignment of progressive add lenses in eyeglasses;
b. Fitting said subject with said eyeglasses;
c. Positioning said subject in front of a chart having characters;
d. Establishing the visual axis in said subject's left eye by obscuring vision in said subject's right eye, adjusting the position of said subject relative to said chart by-side-to-side motion, and establishing the position where said characters are most clearly distinguished by subject's left eye;
e. Establishing the visual axis in said subject's right eye by obscuring vision in said subject's left eye, adjusting the position of said subject relative to said chart by-side-to-side motion, and establishing the position where said characters are most clearly distinguished by subject's right eye;
f. Establishing the optical axis in said subject's left eye and right eye;
g. Comparing the visual axis to the optical axis to determine if a threshold differential exists; and
h. Repositioning at least one of said progressive add lenses to lessen the difference between the visual axis and optical axis if said differential exists.

16. The method of claim 15 wherein said threshold is between approximately 0.10 mm and 10.0 mm when fixation point is approximately 40 cm from subject, or proportional ratios thereof.

17. The method of claim 16 wherein said threshold is between approximately 0.50 mm and 5.0 mm when fixation point is approximately 33.0 mm to 500 mm from subject.

\* \* \* \* \*